United States Patent
Chen et al.

(10) Patent No.: US 11,802,299 B2
(45) Date of Patent: Oct. 31, 2023

(54) ENZYME-CATALYZED METHOD FOR SYNTHESIZING (2S, 3R)-2-SUBSTITUTED AMINOMETHYL-3-HYDROXYBUTYRATE

(71) Applicant: Fudan University, Shanghai (CN)

(72) Inventors: Fener Chen, Shanghai (CN); Yuan Tao, Shanghai (CN); Zedu Huang, Shanghai (CN); Dang Cheng, Shanghai (CN); Ge Meng, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/545,963

(22) Filed: Dec. 8, 2021

(65) Prior Publication Data
US 2022/0090151 A1 Mar. 24, 2022

(30) Foreign Application Priority Data
Jun. 8, 2021 (CN) .......................... 202110634136.8

(51) Int. Cl.
*C12P 13/00* (2006.01)

(52) U.S. Cl.
CPC ..... *C12P 13/001* (2013.01); *C12Y 101/01184* (2013.01)

(58) Field of Classification Search
CPC ..... C12Y 101/01184; C12Y 101/01047; C12P 13/001; C12P 41/002; C12N 15/70
USPC ........................................................ 435/128
See application file for complete search history.

(56) References Cited

U.S. PATENT DOCUMENTS 4,927,507 A    5/1990    Schneider et al.

FOREIGN PATENT DOCUMENTS

CN    1940080 B    7/2010
CN    1940079 B    10/2010

OTHER PUBLICATIONS

Wu. et al. CN 104846025, 2015, pp. 1-11.*
Xiang, Chen, Zhi-Qiang, Liu, Jian-Feng, & Huang, et al. (2015). Asymmetric synthesis of optically active methyl-2-benzamido-methyl-3-hydroxy-butyrate by robust short-chain alcohol dehydrogenases from burkholderia gladioli[J]. Chem. Commun. 51, 12328-12331.

* cited by examiner

*Primary Examiner* — Robert B Mondesi
*Assistant Examiner* — Mohammad Y Meah (57) ABSTRACT

An enzyme-catalyzed method of synthesizing (2S,3R)-2-substituted aminomethyl-3-hydroxybutyrate, including: preparing engineered bacteria containing a carbonyl reductase SsCR-encoding gene; preparing a resting cell suspension of the engineered bacteria; preparing a culture containing carbonyl reductase; and mixing the culture containing carbonyl reductase with substrate 2-substituted aminomethyl-3-one butyrate, glucose dehydrogenase, a cosolvent, glucose and a cofactor followed by asymmetric carbonyl reduction to obtain (2S,3R)-2-substituted aminomethyl-3-hydroxybutyrate. The amino acid sequence of the carbonyl reductase is shown in SEQ ID NO.1.

10 Claims, 5 Drawing Sheets

Specification includes a Sequence Listing.

SEQUENCE LISTING

```
<160> NUMBER OF SEQ ID NOS: 1

<210> SEQ ID NO 1
<211> LENGTH: 343
<212> TYPE: PRT
<213> ORGANISM: Artificial Sequence
<220> FEATURE:
<223> OTHER INFORMATION: synthetic

<400> SEQUENCE: 1

Met Ala Lys Ile Asp Asn Ala Val Leu Pro Glu Gly Ser Leu Val Leu
1               5                   10                  15

Val Thr Gly Ala Asn Gly Phe Val Ala Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Thr Pro Ser Val Lys Arg Phe
        115                 120                 125
```

```
Val Leu Thr Ser Ser Thr Val Ser Ala Leu Ile Pro Lys Pro Asn Val
            130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
            195                 200                 205

Thr Ile Gly Thr Ile Phe Asp Pro Glu Thr Gln Ser Gly Ser Thr Ser
            210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
                245                 250                 255

His Leu Gly Cys Leu Val Leu Pro Gln Ile Glu Arg Arg Arg Val Tyr
            260                 265                 270

Gly Thr Ala Gly Thr Phe Asp Trp Asn Thr Val Leu Ala Thr Phe Arg
            275                 280                 285

Lys Leu Tyr Pro Ser Lys Thr Phe Pro Ala Asp Phe Pro Asp Gln Gly
            290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340
```

ENZYME-CATALYZED METHOD FOR SYNTHESIZING (2S, 3R)-2-SUBSTITUTED AMINOMETHYL-3-HYDROXYBUTYRATE

CROSS-REFERENCE TO RELATED APPLICATIONS

This application claims the benefit of priority from Chinese Patent Application No. 202110634136.8, filed on Jun. 8, 2021. The content of the aforementioned application, including any intervening amendments thereto, is incorporated herein by reference in its entirety.

TECHNICAL FIELD

This application relates to biopharmaceutical techniques, and more specifically to an enzyme-catalyzed method for synthesizing (2S,3R)-2-substituted aminomethyl-3-hydroxybutyrate.

BACKGROUND

Carbapenem antibiotics (i.e., penem antibiotics) are a class of widely-used broad-spectrum antibiotic, mainly including imipenem, meropenem and panipenem, and have a considerable market demand. 4-acetoxyazetidin-2-one, abbreviated as 4-AA, is a main raw material for the production of all carbapenem antibiotics. With respect to the synthesis of 4-AA, the asymmetric reduction of 2-substituted aminomethyl-3-one butyrate (II) to (2S,3R)-2-substituted aminomethyl-3-hydroxybutyrate (I) is a key step.

At present, the preparation of (2S,3R)-2-substituted aminomethyl-3-hydroxybutyrate (I) is mainly performed under the catalysis of a transition metal catalyst or an enzyme. Considering that transition metal catalysts are expensive; the related reaction needs to be carried out under high temperature and high pressure conditions; and heavy metal residues are difficult to be removed, the transition metal-catalyzed preparation of (2S,3R)-2-substituted aminomethyl-3-hydroxybutyrate (I) is not suitable for the industrial manufacture. In recent years, the enzyme-catalyzed asymmetric reduction has attracted extensive attentions. However, this process fails to ensure that the synthesized product has the desired configuration (US patent publication No. 4927507A), and has poor enantioselectivity, so that the product generally needs to be subjected to configuration inversion (Chinese patent Nos. 1940079B and 1940080B). Moreover, this process is limited by low substrate concentration (Xiang, Chen, Zhi-Qiang, Liu, Jian-Feng, & Huang, et al. (2015). Asymmetric synthesis of optically active methyl-2-benzamido-methyl-3-hydroxy-butyrate by robust short-chain alcohol dehydrogenases from burkholderia gladioli[J]. *Chem. Commun.* 51, 12328-12331), limiting its industrial application.

SUMMARY

An object of the present disclosure is to provide a method for synthesizing (2S,3R)-2-substituted aminomethyl-3-hydroxybutyrate (I) with mild conditions and high stereoselectivity.

Technical solutions of the disclosure are specifically described as follows.

The disclosure provides a method for synthesizing (2S, 3R)-2-substituted aminomethyl-3-hydroxybutyrate, comprising:

(1) preparing engineered bacteria containing a carbonyl reductase SsCR-encoding gene;

(2) preparing a resting cell suspension of the engineered bacteria;

(3) inoculating the resting cell suspension of the engineered bacteria into a kanamycin-containing medium to prepare a supernatant containing carbonyl reductase SsCR; and (4) mixing the supernatant with 2-substituted aminomethyl-3-one butyrate (II), glucose dehydrogenase, a cosolvent, a phosphate-buffered saline, glucose, and a cofactor to obtain a reaction mixture; and subjecting the reaction mixture to an asymmetric carbonyl reduction to obtain the (2S,3R)-2-substituted aminomethyl-3-hydroxybutyrate (I), as shown in the following reaction scheme:

wherein $R^1$ is selected from the group consisting of hydrogen, tert-butoxycarbonyl, benzyloxycarbonyl, trityl, formyl, trifluoroacetyl, benzoyl, mono-substituted benzoyl, poly-substituted benzoyl and heteroaryl formyl; and $R^2$ is selected from the group consisting of $C_1$-$C_{10}$ alkyl, cycloalkyl, phenethyl, substituted phenethyl, phenyl and substituted phenyl; and the carbonyl reductase SsCR has an amino acid sequence as shown in SEQ ID NO. 1, or is a carbonyl reductase that has an amino acid sequence with greater than 80% identity with SEQ ID NO. 1 and maintains a catalytic activity.

In an embodiment, the engineered bacteria contain a plasmid pET28a-SsCR, and a host cell is *Escherichia coli* BL21 (DE3).

In an embodiment, the supernatant is prepared through steps of:

inoculating the resting cell suspension of the engineered bacteria into the kanamycin-containing medium followed by activation on a shaker; when an $OD_{600}$ value reaches 0.6-1.2, adding an inducer followed by continuous culture and centrifugation to collect a cell precipitate; suspending the cell precipitate with a buffered solution to obtain a cell suspension with a cell concentration of 1-20 g/100 mL (i.e., a whole cell concentration of 1%-20%); and subjecting the cell suspension to ultrasonic or compressing disruption followed by centrifugation to obtain the supernatant containing the carbonyl reductase SsCR.

In an embodiment, the inducer is isopropyl β-D-thiogalactoside (IPTG) with a concentration of 0.05-0.8 mM.

In an embodiment, after the inducer is added, the culture is performed at 15° C.-25° C. for 8 h-24 h.

In an embodiment, the buffered solution is a sodium dihydrogen phosphate-disodium hydrogen phosphate solution; and a concentration of the buffered solution is 30-300 mM.

During the above-mentioned reaction process, on one hand, the carbonyl reductase (Ketoreductase, KRED) asymmetrically catalyzes the reduction of 2-substituted aminomethyl-3-one butyrate (II) to produce the (2S,3R)-2-substituted aminomethyl-3-hydroxybutyrate (I) with high stereoisomeric purity, which is accompanied by the conversion of a reduced coenzyme factor NADPH into an oxidized coenzyme factor NADP$^+$, on the other hand, glucose dehydrogenase oxidizes glucose to gluconolactone, and at the same time, the oxidized coenzyme factor NADP$^+$ is consumed to generate the reduced coenzyme factor NADPH, so that a consumption-regeneration closed loop of the coenzyme factor is formed to promote the main reaction.

In an embodiment, in the asymmetric carbonyl reduction, a concentration of the 2-substituted aminomethyl-3-one butyrate (II) is 5 g/L-300 g/L; a concentration of the carbonyl reductase SsCR in the supernatant is 1%-20%; a concentration of the glucose dehydrogenase is 0.1-1 g/L; a concentration of the glucose is 1-600 g/L; and a concentration of the cofactor is 0.01-0.5 mM.

In an embodiment, the asymmetric carbonyl reduction is performed at 20° C.-40° C., and a pH of the phosphate buffered saline is 5.0-8.0. In an embodiment, the asymmetric carbonyl reduction is performed at 25-30° C., and the phosphate buffered saline has a pH of 6.5-7.5 and a concentration of 100-250 mM.

In an embodiment, in the asymmetric carbonyl reduction, the cosolvent is selected from the group consisting of dimethyl sulfoxide, N,N-dimethylformamide, N,N-dimethylacetamide, benzene, toluene, ethylbenzene, chlorobenzene, bromobenzene, n-hexane, cyclohexane, acetonitrile, ethyl acetate, dichloromethane, acetone, 1,2-dichloroethane, methanol, ethanol, isopropanol and a combination thereof. In an embodiment, the cosolvent is methanol, and the methanol is 10% by volume of the reaction mixture.

In an embodiment, in the asymmetric carbonyl reduction, after the 2-substituted aminomethyl-3-one butyrate (II) is monitored by supercritical fluid chromatography (SFC) to be completely consumed, the reaction mixture is subjected to extraction 3-4 times with an equal volume of ethyl acetate, and organic phases are collected, combined, washed twice with saturated sodium chloride, dried with anhydrous sodium sulfate, and subjected to vacuum distillation to remove ethyl acetate to obtain a target product (2S,3R)-2-substituted aminomethyl-3-hydroxybutyrate (I).

Compared to the prior art, the present disclosure has the following beneficial effects.

(1) Engineered bacteria containing carbonyl reductase are constructed and applied to an asymmetric reduction of 2-substituted aminomethyl-3-one butyrate (II) to produce (2S,3R)-2-substituted aminomethyl-3-hydroxybutyrate (I), which provides a new biocatalytic method for the preparation of an important intermediate 4-AA in the synthesis of penem drugs.

(2) The present disclosure employs a carbonyl reductase instead of the expensive metal catalyst to carry out the asymmetric carbonyl reduction, and the entire reaction is carried out under mild conditions, reducing the manufacture cost.

(3) The present disclosure adopts readily-available *Escherichia coli* engineered bacteria to enable the stereoselective reduction of a 2-position carbonyl group of the 4-AA intermediate, and 2- and 3-position stereocenters are constructed. This process has simple operation and excellent enantioselectivity (99% ee) and diastereoselectivity (>25:1 dr), and does not need complicated control. Moreover, this method also enables the complete conversion of the substrate with a concentration up to 300 g/L.

DETAILED DESCRIPTION OF EXAMPLES

Example 1 Construction of Genetically Engineered Bacteria, Induced Expression of Carbonyl Reductase and Purification A plasmid pET28a-SsCR was transformed into a host cell *E. coli* BL21 (DE3). The BL21(DE3)-pET28a-SsCR was inoculated into 5 mL of a kanamycin-containing liquid LB culture medium in a test tube, and activated on a shaker at 37° C. for 8 hours. The activated cells were transferred to a kanamycin-containing liquid LB culture medium in a shake flask at a volume ratio of 1:100, and cultured at 37° C. and 200 rpm for 3 hours. When the OD$_{600}$ reached 0.8, IPTG was added to a final concentration of 0.1 mM to induce the expression of SsCR at 18° C. for 18 h. The cells were collected by centrifugation at 8,500 rpm for 10 min, resuspended with a 100 mM potassium phosphate buffer (pH 7.0), disrupted at an ultrasonic power of 55% for 15 minutes, and centrifuged to obtain an SsCR-containing supernatant.

Example 2 Preparation of (2S,3R)-2-benzamidomethyl-3-hydroxybutyrate (I$_a$) (100 g/L Feed)

(I$_a$)

(II$_a$)

To a 25 mL round-bottom flask were added 1.5 g (400 mM) of 2-benzoylaminomethyl-3-oxobutyrate (II$_a$), 1.5 mL of toluene (10% v/v), 2.378 g of a cosubstrate glucose (158.5 g/L; an equivalence ratio of glucose to 2-benzoylaminomethyl-3-oxobutyrate (II$_a$) was 2:1), a NADP$^+$ solution (a final concentration of 0.2230 g/L (0.3 mM)) and 3 mL of a glucose dehydrogenase (GDH)-containing cell supernatant (20% v/v). The reaction mixture was added with 6 mL of the SsCR-containing supernatant (20% v/v) prepared in Example 1 and 100 mM sodium phosphate buffer (pH=7.0) to a final volume of 15 mL, and adjusted to pH 6.9-7.1 with saturated Na$_2$CO$_3$ solution. Then the reaction mixture was reacted in a 30° C. water bath under stirring at 600 rpm for 33 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 88:1, respectively. The crude product was purified by column chromatography to give 1.43 g of a target product (95% yield).

$^1$H NMR (400 MHz, CDCl$_3$): δ 7.71 (d, J=8.0 Hz, 2H), 7.43 (t, J=8.0 Hz, 1H), 7.33 (t, J=8.0 Hz, 3H), 4.56 (d, J=8.0 Hz, 1H), 3.94-4.01 (m, J=8.0 Hz, 2H), 3.64 (s, 3H), 3.55-3.61 (dt, J=4 Hz, 1H), 2.56-2.60 (m, 1H), 1.19-1.20 (d, J=4 Hz, 3H).

$^{13}$C NMR (400 MHz, CDCl$_3$): δ 173.99, 168.76, 133.73, 131.78, 128.57, 127.07, 65.79, 52.61, 51.98, 38.12, 20.97.

Figure 1:
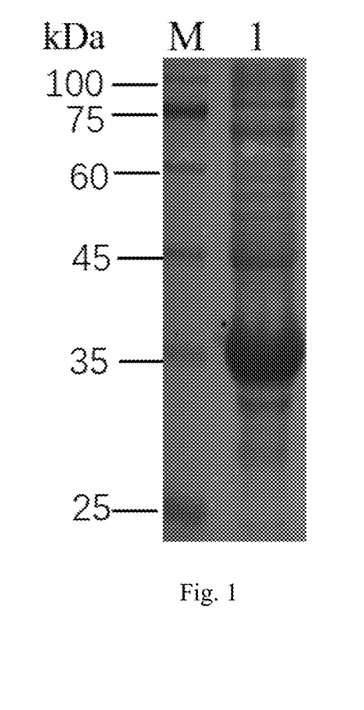
FIG. 1 is an electrophoretogram of a supernatant of crude SsCR expressed by genetically-engineered bacteria under the induction, in which M is nucleic acid Marker; and 1 is the SsCR crude enzyme solution.
Figure 2:
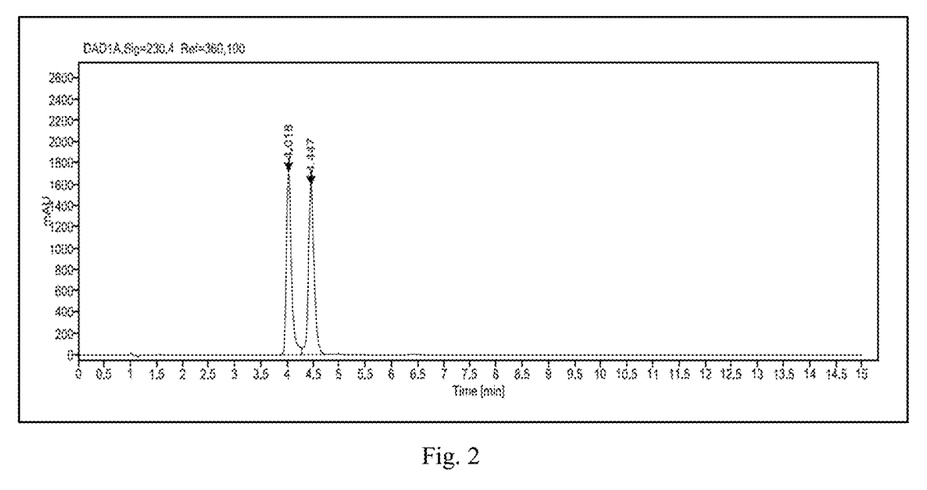
FIG. 2 is an SFC spectrum of a 4-AA intermediate 2-benzoylaminomethyl-3-oxobutyrate.
Figure 3:
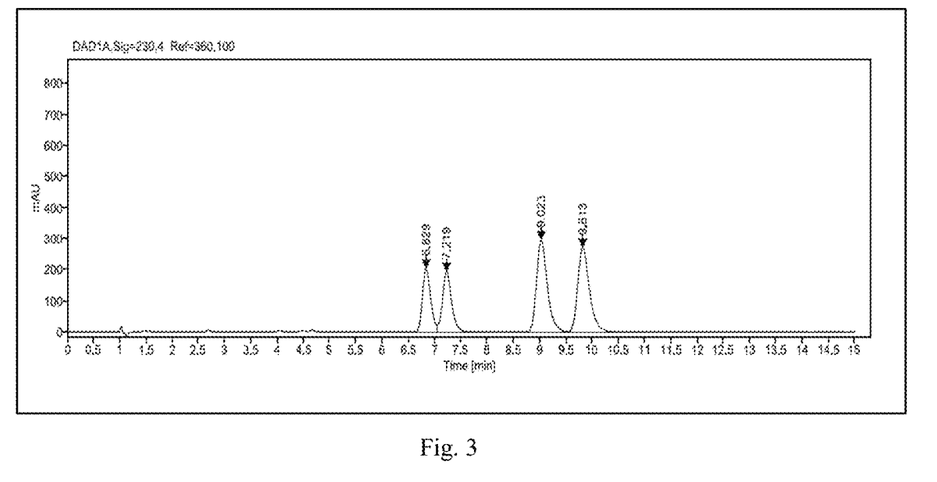
FIG. 3 is an SFC spectrum of Racemic-2-benzoylaminomethyl-3-hydroxybutyrate.
Figure 4:
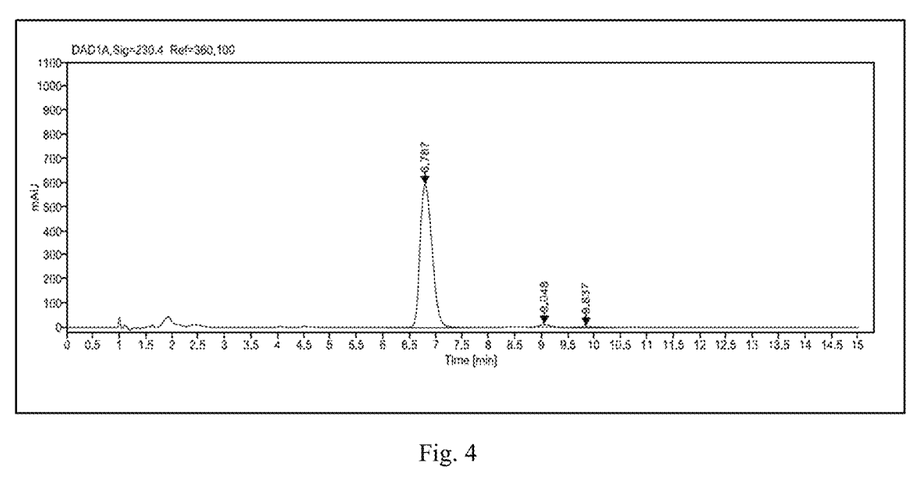
FIG. 4 is an SFC spectrum of (2S,3R)-2-benzamidomethyl-3-hydroxybutyrate produced from an enzyme-catalyzed carbonyl reduction for the measurement of ee and dr.
Figure 5:
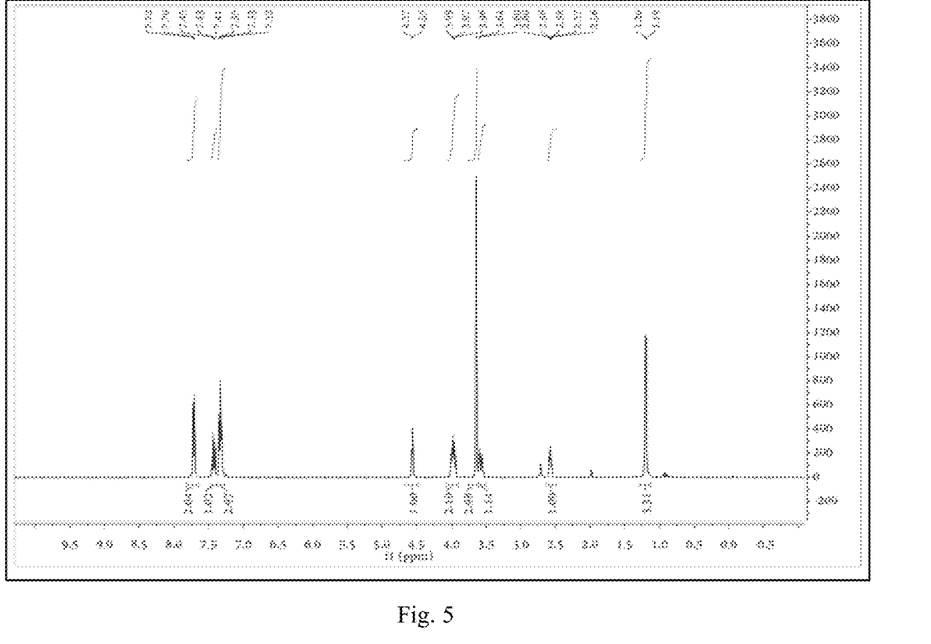
FIG. 5 is a $^1$H NMR spectrum of (2S,3R)-2-benzoylaminomethyl-3-hydroxybutyrate.
Figure 6:
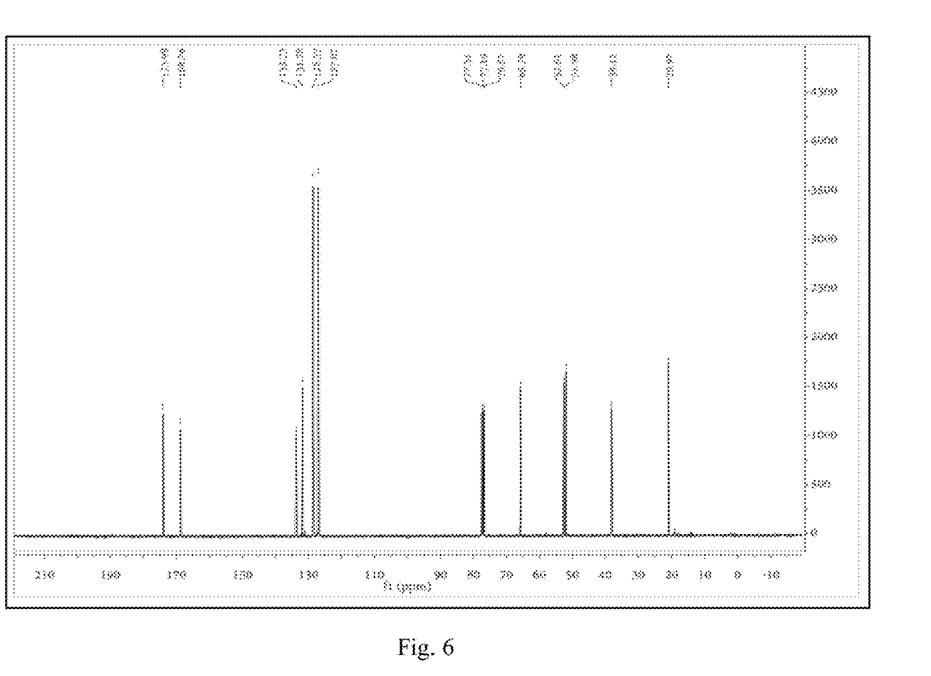
FIG. 6 is a $^{13}$C NMR spectrum of (2S,3R)-2-benzoylaminomethyl-3-hydroxybutyrate.

SFC analysis conditions were set as follows: chromatographic column: chiralpak AD-H (4.6 mm×250 mm); mobile phase: CO$_2$/IPA=90:10; flow rate: 3 mL/min; injection volume: 10 μL; detection wavelength: 230 nm; column temperature: 30° C.; and SFC back pressure: 140 bar. An SFC spectrum of a racemate raw material 2-benzoylaminomethyl-3-oxobutyrate (II$_a$) was shown in FIG. 2, and the retention time of IL was 4.02 min and 4.45 min. An SFC spectrum of a racemate 2-benzoylaminomethyl-3-hydroxybutyrate was shown in FIG. 3, and the retention time of (2S,3R)-2-benzoylaminomethyl-3-hydroxybutyrate (I$_a$) was 6.83 min. An SFC spectrum of a product obtained from the enzyme-catalyzed carbonyl reduction was shown in FIG. 4, and a main configuration was determined to be (2S,3R)-2-benzoylaminomethyl-3-hydroxybutyrate (I$_a$), which had a retention time of 6.79 min. The $^1$H NMR spectrum and $^{13}$C NMR spectrum of (2S,3R)-2-benzoylaminomethyl-3-hydroxybutyrate (I$_a$) were respectively shown in FIG. 5 and FIG. 6.

Example 3 Preparation of (2S,3R)-2-benzamidomethyl-3-hydroxybutyrate (I$_a$) (300 g/L feed)

To a 250 mL round-bottom flask were added 30 g (1200 mM) of 2-benzoylaminomethyl-3-oxobutyrate (II$_a$), 20 mL of toluene (10% v/v), 59.45 g (3000 mM) of a cosubstrate glucose (595 g/L; and a equivalence ratio of glucose to 2-benzoylaminomethyl-3-oxobutyrate (II$_a$) was 2.5:1), a NADP$^+$ solution (a final concentration of 0.3717 g/L (0.5 mM)) and 20 mL of a glucose dehydrogenase (GDH)-containing cell supernatant (20% v/v). The reaction mixture was added with 60 mL of the SsCR-containing supernatant (20% v/v) prepared in Example 1 and 100 mM sodium phosphate buffer (pH=7.0) to a final volume of 100 mL, and adjusted to pH 6.9-7.1 with saturated Na$_2$CO$_3$ solution. Then the reaction mixture was reacted in a 30° C. water bath under stirring at 600 rpm for 35 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 42:1, respectively. The crude product was added with 100 mL of methyl tert-butyl ether, pulped and recrystallized with 100 mL of toluene to give 29.0 g of a target product (96% yield).

Example 4 Preparation of ethyl (2S,3R)-2-(tert-butoxycarbonyl) aminomethyl-3-hydroxybutyrate (I$_b$)

(I$_b$)

(II$_b$)

To a 50 mL round-bottom flask were added 129.5 mg (20 mM) of ethyl 2-(tert-butoxycarbonyl) aminomethyl-3-oxobutyrate (II$_b$), 2.5 mL of n-hexane (10% v/v), 198.2 mg (40 mM) of a cosubstrate glucose (7.9 g/L; and an equivalence ratio of glucose to the ethyl 2-(tert-butoxycarbonyl) aminomethyl-3-oxobutyrate (II$_b$) was 2:1), a NADP$^+$ solution (a final concentration of 0.0149 g/L (0.02 mM)) and 2 mL of a glucose dehydrogenase (GDH)-containing cell supernatant (20% v/v). The reaction mixture was added with 3 mL of the SsCR-containing supernatant (20% v/v) prepared in Example 1 and 100 mM sodium phosphate buffer (pH=7.0) to a final volume of 25 mL, and adjusted to pH 6.4-6.6 with saturated Na$_2$CO$_3$ solution. Then the reaction mixture was reacted in a 30° C. water bath under stirring at 600 rpm for 12 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 36:1, respectively. The crude product was purified by column chromatography to give 117 mg of a target product (90% yield).

$^1$H NMR (500 MHz, CDCl$_3$): δ4.21 (q, J=11.8 Hz, 2H), 4.19 (s, 1H), 4.09 (m, J=11.4 Hz, 1H), 3.47 (m, J=7.23 Hz, 1), 3.12-3.26 (m, 2H), 1.77 (s, 1H), 1.42 (s, 9H), 1.22 (t, J=11.78 Hz, 3H), 1.13 (d, J=11.4 Hz, 3H).

$^{13}$C NMR (500 MHz, CDCl$_3$): δ 172.53, 158.22, 80.89, 69.03, 61.74, 51.92, 38.36, 28.33, 21.43, 14.68.

Example 5 Preparation of propyl (2S,3R)-2-(benzyloxycarbonyl) aminomethyl-3-hydroxybutyrate (I$_c$)

To a 50 mL round-bottom flask were added 230 mg (30 mM) of propyl 2-(benzyloxycarbonyl)aminomethyl-3-oxobutyrate (II$_c$), 2.5 mL of isopropanol (10% v/v), 297 mg of a cosubstrate glucose (11.88 g/L; and an equivalence ratio of glucose to the propyl 2-(benzyloxycarbonyl)aminomethyl-3-oxobutyrate (II$_c$) was 2:1), a NADP$^+$ solution (a final concentration of 0.0223 g/L (0.03 mM)) and 2.5 mL of a glucose dehydrogenase (GDH)-containing cell supernatant (20% v/v). The reaction mixture was added with 4 mL of the SsCR-containing supernatant (20% v/v) prepared in Example 1 and 100 mM sodium phosphate buffer (pH=7.0) to a final volume of 25 mL, and adjusted to pH 6.4-6.6 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 37:1, respectively. The crude product was purified by column chromatography to give 218 mg of a target product (94% yield).

$^1$H NMR (500 MHz, CDCl$_3$): δ 7.68 (s, 1H), 7.33 (s, 5H), 5.50 (s, 2H), 4.29 (s, 1H), 4.16 (tt, J=22.7, 11.4 Hz, 1H), 4.04 (t, J=9.5 Hz, 2H), 3.48 (dd, J=24.8, 7.4 Hz, 1H), 3.22 (dd, J=24.8, 7.4 Hz, 1H), 2.91 (dt, J=21.6, 7.4 Hz, 1H), 1.73 (m, 2H), 1.13 (d, J=11.4 Hz, 3H), 1.01 (t, J=13.4 Hz, 1H).

$^{13}$C NMR (500 MHz, CDCl$_3$): δ 172.31, 157.31, 137.77, 129.12, 128.30, 128.23, 69.03, 67.48, 67.18, 51.92, 38.36, 22.18, 21.43, 10.60.

Example 6 Preparation of cyclohexyl (2S,3R)-2-formylaminomethyl-3-hydroxybutyrate (I$_d$)

To a 50 mL round-bottom flask were added 150.8 mg (25 mM) of cyclohexyl 2-formylaminomethyl-3-oxobutanoate (II$_d$), 2.5 mL of dichloromethane (10% v/v), 247.7 mg of a cosubstrate glucose (9.90 g/L; and an equivalence ratio of glucose to the cyclohexyl 2-formylaminomethyl-3-oxobutanoate (II$_d$) was 2:1), a NADP$^+$ solution (a final concentration of 0.0223 g/L (0.03 mM)) and 2.5 mL of a glucose dehydrogenase (GDH)-containing cell supernatant (20% v/v). The reaction mixture was added with 4 mL of the SsCR-containing supernatant (20% v/v) prepared in Example 1 and 100 mM sodium phosphate buffer (pH=7.0) to a final volume of 25 mL, and adjusted to pH 7.4-7.6 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 41:1, respectively. The crude product was purified by column chromatography to give 138 mg of a target product (91% yield).

$^1$H NMR (500 MHz, CDCl$_3$): δ 8.06 (s, 1H), 5.75 (s, 1H), 4.52-4.37 (m, 2H), 4.04 (t, J=9.5 Hz, 2H), 3.48 (dd, J=24.8, 12.9 Hz, 1H), 3.22 (dd, J=24.8, 12.7 Hz, 1H), 2.78 (td, J=12.8, 1 Hz, 1H), 1.80-1.71 (m, 2H), 1.70 (s, 1H), 1.66-1.58 (m, 3H), 1.27-1.16 (m, 5H), 1.13 (d, J=11.4 Hz, 3H).

$^{13}$C NMR (500 MHz, CDCl$_3$): δ 173.93, 164.14, 76.48, 69.03, 52.37, 38.49, 30.81, 25.90, 24.57, 21.43.

Example 7 Preparation of benzyl (2S,3R)-2-tritylaminomethyl-3-hydroxybutyrate (I$_c$)

(I$_e$)

(II$_e$)

To a 50 mL round-bottom flask were added 289.7 mg (25 mM) of benzyl 2-tritylaminomethyl-3-oxobutyrate (II$_e$), 2.5 mL of isopropanol (10% v/v), 247.7 mg of a cosubstrate glucose (9.90 g/L; and an equivalence ratio of glucose to the benzyl 2-tritylaminomethyl-3-oxobutyrate (II$_e$) was 2:1), a NADP$^+$ solution (a final concentration of 0.0223 g/L (0.03 mM)) and 3 mL of a glucose dehydrogenase (GDH)-containing cell supernatant (20% v/v). The reaction mixture was added with 6 mL of the SsCR-containing supernatant (20% v/v) prepared in Example 1 and 100 mM sodium phosphate buffer (pH=7.0) to a final volume of 25 mL, and adjusted to pH 6.4-6.6 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 37:1, respectively. The crude product was purified by column chromatography to give 265 mg of a target product (91% yield).

$^1$H HMR (500 MHz, CDCl$_3$): δ 7.32 (m, 20H), 5.33 (s, 2H), 4.20 (qd, J=11.4, 1.4 Hz, 1H), 3.06 (dd, J=24.2, 12.3 Hz, 1H), 2.81 (dd, J=24.3, 12.5 Hz, 1H) 2.76 (s, 1H), 2.71 (td, J=12.5, 1.5 Hz, 1H), 2.01 (s, 1H), 1.13 (d, J=11.4 Hz, 3H).

$^{13}$C NMR (500 MHz, CDCl$_3$): δ 172.55, 144.46, 137.77, 129.12, 128.96, 128.90, 128.38, 128.30, 128.23, 72.14, 69.03, 67.16, 52.13, 42.18, 21.43.

Example 8 Preparation of p-chlorophenethyl (2S,3R)-2-trifluoroformylaminomethyl-3-hydroxybutyrate (I$_f$)

(I$_f$)

(II$_f$)

To a 50 mL round-bottom flask were added 914.3 mg (100 mM) of p-chlorophenethyl 2-trifluoroformylaminomethyl-3-oxobutyrate (II$_f$), 2.5 mL of toluene (10% v/v), 990.9 mg of a cosubstrate glucose (39.63 g/L; and an equivalence ratio of glucose to the p-chlorophenethyl 2-trifluoroformylaminomethyl-3-oxobutyrate (II$_f$) was 2:1), a NADP$^+$ solution (a final concentration of 0.0743 g/L (0.1 mM)) and 3 mL of a glucose dehydrogenase (GDH)-containing cell supernatant (20% v/v). The reaction mixture was added with 6 mL of the SsCR-containing supernatant (20% v/v) prepared in Example 1 and 100 mM sodium phosphate buffer (pH=7.0) to a final volume of 25 mL, and adjusted to pH 6.9-7.1 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 29:1, respectively. The crude product was purified by column chromatography to give 772 mg of a target product (84% yield).

$^1$H NMR (500 MHz, CDCl$_3$): δ 7.39-7.28 (m, 2H), 7.24-7.15 (m, 2H), 6.17 (s, 1H), 4.59 (dq, J=22.7, 11.4 Hz, 1H), 4.42 (t, J=15.0 Hz, 2H), 3.71 (dd, J=24.8, 14.1 Hz, 1H), 3.45 (dd, J=24.7, 14.1 Hz, 1H), 2.96 (t, J=15.0 Hz, 2H), 2.76 (dt, J=21.8, 14.1 Hz, 1H), 1.65 (s, 1H), 1.13 (d, J=11.4 Hz, 3H).

$^{13}$C NMR (500 MHz, CDCl$_3$): δ 172.31, 159.00 (q, J=32.4 Hz), 139.82, 133.14, 130.53, 128.53, 114.49 (q, J=268.1 Hz), 69.03, 66.61, 51.92, 38.27 (d, J=1.5 Hz), 35.62, 21.43.

Example 9 Preparation of p-methoxyphenethyl (2S, 3R)-2-trifluoroformylaminomethyl-3-hydroxybutyrate (I$_g$)

To a 50 mL round-bottom flask were added 722.6 mg (80 mM) of p-methoxyphenethyl 2-trifluoroformylaminomethyl-3-oxobutyrate (II$_g$), 2.5 mL of toluene (10% v/v), 792.7 mg of a cosubstrate glucose (31.70 g/L; and an equivalence ratio of glucose to the p-methoxyphenethyl 2-trifluoroformylaminomethyl-3-oxobutyrate (II$_g$) was 2:1), a NADP$^+$ solution (a final concentration of 0.0372 g/L (0.05 mM)) and 3 mL of a glucose dehydrogenase (GDH)-containing cell supernatant (20% v/v). The reaction mixture was added with 6 mL of the SsCR-containing supernatant (20% v/v) prepared in Example 1 and 100 mM sodium phosphate buffer (pH=7.0) to a final volume of 25 mL, and adjusted to pH 6.9-7.1 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 35:1, respectively. The crude product was purified by column chromatography to give 610 mg of a target product (84% yield).

$^1$H NMR (500 MHz, CDCl$_3$): δ 7.20-7.16 (m, 2H), 6.88-6.84 (m, 2H), 6.10 (s, 1H), 4.42 (t, J=15.0 Hz, 2H), 4.31 (dq, J=16.7, 11.4 Hz, 1H), 3.79 (s, 3H), 3.71 (dd, J=24.8, 12.4 Hz, 1H), 3.45 (dd, J=24.7, 12.3 Hz, 1H), 2.96 (t, J=15.0 Hz, 2H), 2.81 (dt, J=16.8, 12.4 Hz, 1H), 2.54 (s, 1H), 1.13 (d, J=11.4 Hz, 3H).

$^{13}$C NMR (500 MHz, CDCl$_3$): δ 172.31, 159.13, 158.99 (q, J=32.4 Hz, 1C), 132.02, 130.35, 115.16, 114.48 (q, J=268.1 Hz, 1C), 69.03, 66.61, 56.08, 51.92, 38.27 (d, J=1.5 Hz, 1C), 35.62, 21.43.

Example 10 Preparation of p-methoxyphenethyl (2S,3R)-2-m-bromobenzoylaminomethyl-3-hydroxybutyrate (I$_h$)

To a 50 mL round-bottom flask were added 280.2 mg (25 mM) of p-methoxyphenethyl 2-m-bromobenzoylaminomethyl-3-oxobutyrate (II$_h$), 2.5 mL of ethyl acetate (10% v/v), 247.7 mg of a cosubstrate glucose (9.90 g/L; and an equivalence ratio of glucose to the p-methoxyphenethyl 2-m-bromobenzoylaminomethyl-3-oxobutyrate (II$_h$) was 2:1), a NADP$^+$ solution (a final concentration of 0.0223 g/L (0.03 mM)) and 2 mL of a glucose dehydrogenase (GDH)-containing cell supernatant (20% v/v). The reaction mixture was added with 4 mL of the SsCR-containing supernatant (20% v/v) prepared in Example 1 and 100 mM sodium phosphate buffer (pH=7.0) to a final volume of 25 mL, and adjusted to pH 6.9-7.1 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 35:1, respectively. The crude product was purified by column chromatography to give 265 mg of a target product (94% yield).

$^1$H NMR (500 MHz, CDCl$_3$): δ 8.14 (t, J=3.0 Hz, 1H), 7.89 (dt, J=14.8, 2.9 Hz, 1H), 7.79 (dt, J=14.8, 3.0 Hz, 1H), 7.50 (t, J=14.9 Hz, 1H), 7.22-7.14 (m, 2H), 6.92-6.81 (m, 2H), 6.50 (s, 1H), 4.54 (dq, J=22.9, 11.4 Hz, 1H), 4.42 (t, J=9.8 Hz, 2H), 3.79 (s, 3H), 3.71 (dd, J=24.8, 12.7 Hz, 1H), 3.45 (dd, J=24.7, 12.6 Hz, 1H), 2.96 (t, J=9.9 Hz, 2H), 2.50 (dt, J=21.8, 12.6 Hz, 1H), 1.60 (s, 1H), 1.13 (d, J=11.4 Hz, 3H).

$^{13}$C NMR (500 MHz, CDCl$_3$): δ 172.31, 167.08, 159.14, 135.37, 134.43, 132.48, 132.02, 130.92, 130.35, 127.03, 123.17, 115.16, 69.03, 66.61, 56.08, 51.92, 39.15, 35.62, 21.43.

Example 11 Preparation of 3,4-dimethoxyphenethyl (2S,3R)-2-[(3,4-dibromobenzoyl) amino] methyl-3-hydroxybutyrate (I$_i$)

To a 50 mL round-bottom flask were added 139.3 mg (10 mM) of 3,4-dimethoxyphenethyl 2-[(3,4-dibromobenzoyl) amino]methyl-3-oxobutyrate (II$_i$), 2.5 mL of methanol (10% v/v), 99 mg of a cosubstrate glucose (3.96 g/L; and an equivalence ratio of glucose to the 3,4-dimethoxyphenethyl 2-[(3,4-dibromobenzoyl) amino] methyl-3-oxobutyrate (II$_i$) was 2:1), a NADP$^+$ solution (a final concentration of 0.0074 g/L (0.01 mM)) and 1 mL of a glucose dehydrogenase (GDH)-containing cell supernatant (20% v/v). The reaction mixture was added with 2 mL of the SsCR-containing supernatant (20% v/v) prepared in Example 1 and 100 mM sodium phosphate buffer (pH=7.0) to a final volume of 25 mL, and adjusted to pH 7.4-7.6 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 43:1, respectively. The crude product was purified by column chromatography to give 133 mg of a target product (95% yield).

$^1$H NMR (500 MHz, CDCl$_3$): δ 8.06 (d, J=3.0 Hz, 1H), 7.90 (dd, J=14.9, 3.0 Hz, 1H), 7.72 (d, J=14.9 Hz, 1H), 6.86 (dd, J=14.9, 2.8 Hz, 1H), 6.79 (d, J=15.0 Hz, 1H), 6.76 (d, J=2.8 Hz, 1H), 6.38 (s, 1H), 4.51-4.40 (m, 3H), 3.83 (s, 3H), 3.75 (s, 3H), 3.72-3.67 (m, 1H), 3.45 (dd, J=24.7, 11.5 Hz, 1H), 2.96 (t, J=9.0 Hz, 2H), 2.38 (dt, J=21.7, 11.5 Hz, 1H), 1.45 (s, 1H), 1.13 (d, J=11.4 Hz, 3H).

$^{13}$C NMR (500 MHz, CDCl$_3$): δ 172.31, 167.08, 149.37, 148.30, 136.94, 134.28, 133.68, 133.15, 131.47, 128.98, 125.78, 122.75, 114.77, 113.60, 69.03, 66.61, 56.83, 51.92, 39.15, 36.11, 21.43.

Example 12 Preparation of phenyl (2S,3R)-2-[(3-pyridinecarbonyl) amino]methyl-3-hydroxybutyrate

To a 50 mL round-bottom flask were added 312.3 mg (40 mM) of phenyl 2-[(3-pyridinecarbonyl) amino] methyl-3-oxobutyrate (II$_j$), 2.5 mL of dimethyl sulfoxide (10% v/v), 396.3 mg of a cosubstrate glucose (15.85 g/L; and an equivalence ratio of glucose to the phenyl 2-[(3-pyridinecarbonyl) amino] methyl-3-oxobutyrate (II$_j$) was 2:1), a NADP$^+$ solution (a final concentration of 0.0372 g/L (0.05 mM)) and 2 mL of a glucose dehydrogenase (GDH)-containing cell supernatant (20% v/v). The reaction mixture was added with 3.5 mL of the SsCR-containing supernatant (20% v/v) prepared in Example 1 and 100 mM sodium phosphate buffer (pH=7.0) to a final volume of 25 mL, and adjusted to pH 7.4-7.6 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 30:1, respectively. The crude product was purified by column chromatography to give 273 mg of a target product (87% yield).

$^1$H NMR (500 MHz, CDCl$_3$): δ 9.00-8.86 (m, 1H), 8.78-8.74 (m, 1H), 8.04 (dt, J=15.0, 3.0 Hz, 1H), 7.47-7.33 (m, 4H), 7.16-6.98 (m, 2H), 6.25 (s, 1H), 4.28-4.20 (m, 1H), 3.51-3.41 (m, 1H), 3.32-3.25 (m, 1H), 3.22 (dd, J=27.1, 7.8 Hz, 1H), 2.55 (s, 1H), 1.13 (d, J=11.4 Hz, 3H).

$^{13}$C NMR (500 MHz, CDCl$_3$): δ 175.66, 166.70, 152.72, 151.88, 151.35, 135.65, 131.94, 129.99, 125.69, 123.49, 122.16, 69.03, 50.77, 39.15, 21.43.

Example 13 Preparation of p-chlorophenyl (2S,3R)-2-[(3-furoyl) amino]methyl-3-hydroxybutyrate (I$_k$)

To a 50 mL round-bottom flask were added 251.8 mg (30 mM) of p-chlorophenyl 2-[(3-furoyl) amino] methyl-3-oxobutanoate (II$_k$), 2.5 mL of cyclohexane (10% v/v), 297.3 mg of a cosubstrate glucose (used herein was glucose monohydrate with a molecular weight of 198.17; molecular weight of anhydrous glucose: 180.16; 11.89 g/L; and an equivalence ratio of glucose to the p-chlorophenyl 2-[(3-furoyl) amino] methyl-3-oxobutanoate (II$_k$) was 2:1), a NADP$^+$ solution (a final concentration of 0.0297 g/L (0.04 mM)) and 2 mL of a glucose dehydrogenase (GDH)-containing cell supernatant (20% v/v). The reaction mixture was added with 4 mL of the SsCR-containing supernatant (20% v/v) prepared in Example 1 and 100 mM sodium phosphate buffer (pH=7.0) to a final volume of 25 mL, and adjusted to pH 6.9-7.1 with saturated Na$_2$CO$_3$ solution. Then the reaction mixture was reacted in a 30° C. water bath under stirring at 600 rpm for 24 hours. After the reaction was completed, the reaction product was subjected to extraction 3 times with ethyl acetate.

Organic phases were combined, washed with saturated sodium chloride, dried with anhydrous sodium sulfate and concentrated to obtain a crude product, of which the ee value and dr value were measured by SFC to be 99:1 and 36:1, respectively. The crude product was purified by column chromatography to give 225 mg of a target product (89% yield).

$^1$H NMR (500 MHz, CDCl$_3$): δ 8.63 (t, J=2.9 Hz, 1H), 7.40 (s, 4H), 7.20-7.15 (m, 2H), 6.37 (s, 1H), 4.50 (dq, J=22.7, 11.4 Hz, 1H), 3.48 (dd, J=24.7, 12.3 Hz, 1H), 3.22 (dd, J=24.7, 12.3 Hz, 1H), 2.69 (dt, J=21.6, 12.3 Hz, 1H), 1.46 (s, 1H), 1.13 (d, J=11.4 Hz, 3H).

$^{13}$C NMR (500 MHz, CDCl$_3$): δ 175.66, 166.26, 150.34, 144.63, 142.99, 131.56, 129.93, 123.64, 122.75, 107.89, 69.03, 50.77, 38.62, 21.43.

What is claimed is:

1. A method of synthesizing (2S,3R)-2-substituted aminomethyl-3-hydroxybutyrate, comprising:

(1) preparing engineered bacteria containing a a carbonyl reductase SsCR-encoding gene;

(2) preparing a resting cell suspension of the engineered bacteria;

(3) inoculating the resting cell suspension of the engineered bacteria into a kanamycin-containing medium to prepare a supernatant containing carbonyl reductase SsCR; and (4) mixing the supernatant with 2-substituted aminomethyl-3-one butyrate (II), glucose dehydrogenase, a cosolvent, a phosphate-buffered saline, glucose and a cofactor to obtain a reaction mixture; and subjecting the reaction mixture to an asymmetric carbonyl reduction to obtain the (2S,3R)-2-substituted aminomethyl-3-hydroxybutyrate (I), as shown in the following reaction scheme:

wherein $R^1$ is selected from the group consisting of hydrogen, tert-butoxycarbonyl, benzyloxycarbonyl, trityl, formyl, trifluoroacetyl, benzoyl, mono-substituted benzoyl, poly-substituted benzoyl and heteroaryl formyl; and $R^2$ is selected from the group consisting of $C_1$-$C_{10}$ alkyl, cycloalkyl, phenethyl, substituted phenethyl, phenyl and substituted phenyl; and the carbonyl reductase SsCR comprises the amino acid sequence of SEQ ID NO:1.

2. The method of claim 1, wherein the engineered bacteria contain a plasmid pET28a-SsCR, and a host cell is *Escherichia coli* BL21 (DE3).

3. The method of claim 2, wherein the supernatant is prepared through steps of:
inoculating the resting cell suspension of the engineered bacteria into the kanamycin-containing medium followed by activation on a shaker; when an $OD_{600}$ value reaches 0.6-1.2, adding an inducer followed by continuous culture and centrifugation to collect a cell precipitate; suspending the cell precipitate with a buffered solution to obtain a cell suspension with a cell concentration of 1-20 g/100 mL; and subjecting the cell suspension to ultrasonic or compressing disruption followed by centrifugation to obtain the supernatant containing the carbonyl reductase SsCR.

4. The method of claim 3, wherein the inducer is isopropyl β-D-thiogalactoside (IPTG) with a concentration of 0.05-0.8 mM.

5. The method of claim 4, wherein after the inducer is added, the culture is performed at 15° C.-25° C. for 8 h-24 h.

6. The method of claim 3, wherein the buffered solution is a sodium dihydrogen phosphate-disodium hydrogen phosphate solution; and a concentration of the buffered solution is 30 mM-300 mM.

7. The method of claim 1, wherein in the asymmetric carbonyl reduction, a concentration of the 2-substituted aminomethyl-3-one butyrate (II) is 5-300 g/L; a concentration of the carbonyl reductase SsCR in the supernatant is 1%-20%; a concentration of the glucose dehydrogenase is 0.1-1 g/L; a concentration of the glucose is 1-600 g/L; and a concentration of the cofactor is 0.01-0.5 mM.

8. The method of claim 7, wherein the asymmetric carbonyl reduction is performed at 20° C.-40° C.; and a pH of the phosphate buffered saline is 5.0-8.0.

9. The method of claim 8, wherein in the asymmetric carbonyl reduction, the cosolvent is selected from the group consisting of dimethyl sulfoxide, N,N-dimethylformamide, N,N-dimethylacetamide, benzene, toluene, ethylbenzene, chlorobenzene, bromobenzene, n-hexane, cyclohexane, acetonitrile, ethyl acetate, dichloromethane, acetone, 1,2-dichloroethane, methanol, ethanol, isopropanol and a combination thereof.

10. The method of claim 9, wherein in the asymmetric carbonyl reduction, after the 2-substituted aminomethyl-3-one butyrate (II) is monitored by supercritical fluid chromatography (SFC) to be completely consumed, the reaction mixture is subjected to extraction 3-4 times with an equal volume of ethyl acetate, and organic phases are collected, combined, washed twice with saturated sodium chloride, dried with anhydrous sodium sulfate, and subjected to vacuum distillation to remove ethyl acetate to obtain a target product (2S,3R)-2-substituted aminomethyl-3-hydroxybutyrate (I).

\* \* \* \* \*